United States Patent
Johnston et al.

(10) Patent No.: US 6,756,062 B2
(45) Date of Patent: Jun. 29, 2004

(54) PREPARATION OF DRUG PARTICLES USING EVAPORATION PRECIPITATION INTO AQUEOUS SOLUTIONS

(75) Inventors: Keith P. Johnston, Austin, TX (US); Robert O. Williams, Austin, TX (US); Timothy J. Young, Midland, MI (US); Xiaoxia Chen, Austin, TX (US)

(73) Assignee: Board of Regents University of Texas System, Austin, TX (US)

( * ) Notice: Subject to any disclaimer, the term of this patent is extended or adjusted under 35 U.S.C. 154(b) by 0 days.

(21) Appl. No.: 09/808,332

(22) Filed: Mar. 14, 2001

(65) Prior Publication Data

US 2002/0081334 A1 Jun. 27, 2002

Related U.S. Application Data (60) Provisional application No. 60/245,479, filed on Nov. 3, 2000.

(51) Int. Cl.[7] .................................................. A61K 9/16
(52) U.S. Cl. ....................................... 424/489; 424/497
(58) Field of Search ................................ 424/489, 497, 424/490

(56) References Cited

U.S. PATENT DOCUMENTS

| | | | |
|---|---|---|---|
| 5,145,684 A | 9/1992 | Liversidge et al. | 424/489 |
| 5,795,594 A | 8/1998 | York et al. | 424/489 |
| 5,851,453 A | 12/1998 | Hanna et al. | 264/5 |
| 5,985,248 A | 11/1999 | Gordon et al. | 424/46 |
| 6,001,336 A | 12/1999 | Gordon | 424/46 |
| 6,077,543 A | 6/2000 | Gordon et al. | 424/489 |

FOREIGN PATENT DOCUMENTS

| | | |
|---|---|---|
| WO | WO 98/29096 | 7/1998 |

*Primary Examiner*—Jyothsna Venkat (57) ABSTRACT

A method for preparing poorly water soluble drug particles is disclosed. The method comprises dissolving a drug in at least one organic solvent to form a drug/organic mixture, spraying the drug/organic mixture into an aqueous solution, and concurrently evaporating the organic solvent in the presence of the aqueous solution to form an aqueous dispersion of the drug particles. The resulting drug particles are in the nanometer to micrometer size range and show enhanced dissolution rates and reduced crystallinity when compared to the unprocessed drug.

25 Claims, 4 Drawing Sheets

PREPARATION OF DRUG PARTICLES USING EVAPORATION PRECIPITATION INTO AQUEOUS SOLUTIONS

This application claims the benefit of provisional application, U.S. Serial No. 60/245,479, filed Nov. 3, 2000.

FIELD OF THE INVENTION

The present invention relates to drug particles and methods for their preparation. More particularly, the present invention relates to the preparation of drug particles utilizing evaporative precipitation into aqueous solutions.

BACKGROUND OF THE INVENTION

Bioavailability is a term meaning the degree to which a drug becomes available to the target tissue after being administered to the body. Poor bioavailability is a significant problem encountered in the development of pharmaceutical compositions, particularly those containing an active ingredient that is poorly soluble in water. Poorly water soluble drugs tend to be eliminated from the gastrointestinal tract before being absorbed into the circulation.

It is known that the rate of dissolution of a particulate drug can increase with increasing surface area, that is, decreasing particle size. Efforts have been made to control the size and size range of drug particles in pharmaceutical compositions. For example, wet milling techniques have been used, as described in U.S. Pat. No. 5,145,684. However, such wet milling techniques exhibit problems associated with contamination from the grinding media. It is difficult to produce highly uniform submicron particles with wet milling and solids milling, and handling can be time consuming. Moreover, exposing a drug substance to mechanical shear or high temperatures for prolonged periods can cause the drug to lose its activity.

Spray drying into vapor is another method used to form micron sized drug particles. Spray drying is used commonly to formulate dry pharmaceutical powder. In most cases, either hydrophilic drugs in aqueous solution or poorly water soluble drugs in organic solution are sprayed, which approaches do not offer a means to simultaneously spray a poorly water soluble drug and water soluble excipient.

U.S. Pat. No. 5,985,248 teaches dissolving a hydrophilic excipient, or stabilizer, and a hydrophobic drug in a cosolvent system such as water:ethanol, and spray drying the system into vapor. U.S. Pat. No. 6,001,336 teaches suspending a hydrophobic drug in an aqueous solution containing a hydrophilic stabilizer, and spray drying the suspension into vapor. U.S. Pat. No. 6,077,543 and WO 98/29096 teach atomizing an organic and an aqueous solution together into a vapor. In all of these teachings, drug particles in the micron size range are formed. It is difficult to produce sub-micron particles by these technique due to growth of the drug particles during the solvent evaporation. As the water evaporates it will no longer solvate hydrophilic stabilizers. Solvation of the stabilizer is needed for it to be able to prevent growth of the drug particles. As a result, growth of the drug particles is not likely to be inhibited by the stabilizer and the particle size is typically greater than 1 micron. Moreover, in all of these teachings, the precipitation of surfactant and stabilizers occur simultaneously in the coaxial nozzle, and it is much more difficult to control the particle morphology. Furthermore, in all of these teachings, the useful excipients are sugars, salts, pectin and citric acid, which are not good stabilizers for preventing growth of particles during the spray process.

U.S. Pat. Nos. 5,795,594 and 5,851,453 teach the use of compressed fluid antisolvents to form drug particles in the micron-size range. This process has been called Precipitation using Compressed Antisolvents (PCA), Solution-Enhanced Dispersion of Solids (SEDS) and Supercritical AntiSolvent process (SAS). In most cases this process does not utilize water due to the low solubility of water in compressed carbon dioxide, so that it is difficult to use water-soluble excipients with this process. However, in some cases, this process is able to use water by flowing an organic drug solution, an aqueous solution and a second organic solvent such as ethanol into compressed carbon dioxide. The ethanol is needed to extract the water into the CO2 phase. In this process it is difficult to control the particle size due to the complexity of the mixing of the three streams in the jet. Also, the particles must be recovered from a high pressure vessel, and high ratios of CO2 to drug are necessary. Moreover, as the water contacts CO2, the pH in the water reaches about 3, which can be detrimental to drug stability and interactions with excipients.

Young et al., *Rapid Expansion from Supercritical to Aqueous Solution to Produce Submicron Suspensions of Water-Insoluble Drugs*, Biotechnol. Prog. 2000, 16, 402–407, teach the formation of poorly water soluble drug particles by rapid expansion of supercritical fluid solutions into water. The supercritical fluid was carbon dioxide above its critical temperature. The solubility of drugs in carbon dioxide and other supercritical fluids such as ethane and propane is typically very small. It is difficult to add water soluble stabilizers and excipients in spray antisolvent processes (PCA, SAS or SEDS) into carbon dioxide due to the low solubility of water in CO2. Reverchon E., *Supercritical Antisolvent Precipitation of Micro-and Nano-particles*, J. Supercrit. Fluid., 1999, 15, 1–21. These antisolvent processes require large ratios of carbon dioxide to drug and the use of a high pressure vessel for recovery of product. Even when an aqueous and two organic solutions are sprayed through a coaxial nozzle, the process is subject to many of the limitations discussed above for spray drying organic and aqueous phases through coaxial nozzles. As the water dissolves into the ethanol-carbon dioxide mixture, it is no longer available to solvate stabilizers to prevent particle growth. Therefore this process is limited to relatively few drugs.

It would be an advantage in the art of preparation of drug particles to provide a method which allows for easy control of particle size and morphology and which is applicable to a wide breadth of drug substances.

SUMMARY OF THE INVENTION

In one aspect, the present invention is a method for preparing poorly water soluble drug particles comprising the steps of dissolving a drug in at least one organic solvent to form a drug/organic mixture; spraying the drug/organic mixture into an aqueous solution; and concurrently evaporating the organic solvent in the presence of the aqueous solution to form an aqueous dispersion of the drug particles.

In a second aspect, the present invention is poorly water soluble drug particles having an average particle diameter of from 50 nanometers to 20 microns, the drug particles being prepared by a process comprising the steps of dissolving the drug in at least one organic solvent to form a drug/organic mixture; spraying the drug/organic mixture into an aqueous solution; and concurrently evaporating the organic solvent in the presence of the aqueous solution to form an aqueous dispersion of the drug particles.

The present invention utilizes evaporative precipitation into aqueous solutions (EPAS) to form micron to sub-micron sized drug particles, leading to increased bioavailability relative to larger particles. The process of the present invention has applicability to a wide range of drug substances as several solvents may be chosen to dissolve the drug. The ability to utilize poorly soluble drugs and water soluble stabilizers/excipients offers the ability to form submicron particles that have high dissolution rates in aqueous media. The present invention also offers the ability to better control the resulting particle size and morphology relative to techniques described in the above identified prior art. Moreover, the present invention often produces particles having reduced crystallinity as compared to the bulk, unprocessed drug, which enhances dissolution.

DETAILED DESCRIPTION OF THE INVENTION

Figure 1:
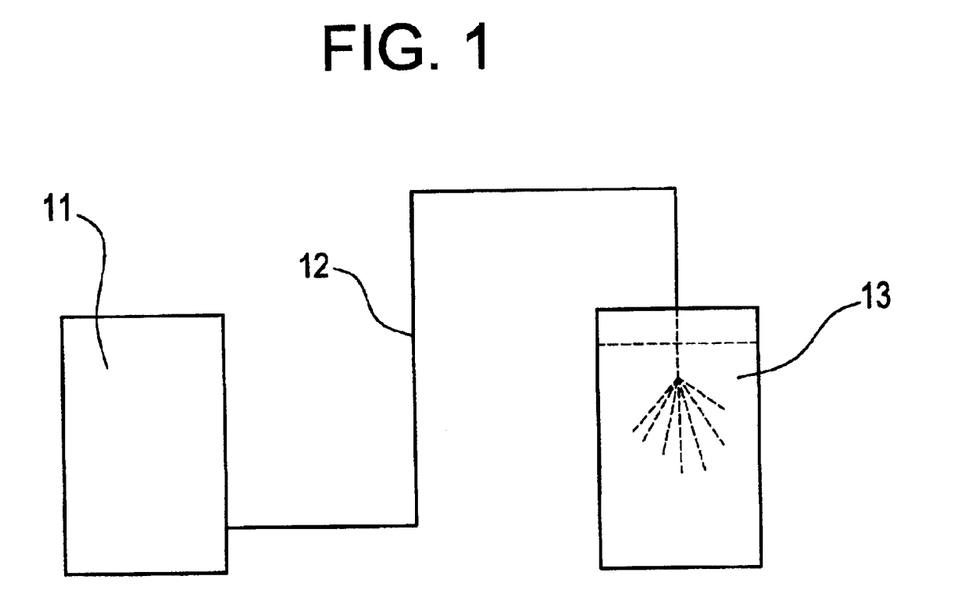
FIG. 1 is a schematic diagram illustrating one embodiment of the process of the present invention.

FIG. 1 is a schematic diagram illustrating one embodiment of an apparatus useful for the process of the present invention. As shown, tank 11 contains a drug/organic mixture. The drug/organic mixture is formed by dissolving a drug in at least one organic solvent. The resulting drug/organic mixture can be a solution, an emulsion or a microemulsion.

The drug which can be used in the process of the present invention can be any poorly water soluble drug. Suitable drug substances can be selected from a variety of known classes of drugs including, for example, analgesics, anti-inflammatory agents, anthelmintics, antianginal agents, antiarrhythmic agents, antibiotics (including penicillins), anticoagulants, antidepressants, antidiabetic agents, antiepileptics, antigonadotropins, antihistamines, antihypertensive agents, antimuscarinic agents, antimycobacterial agents, antineoplastic agents, immunosuppressants, antithyroid agents, antiviral agents, anxiolytic sedatives (hypnotics and neuroleptics), astringents, beta-adrenoceptor blocking agents, blood products and substitutes, cardiacinotropic agents, contrast media, corticosterioids, cough suppressants (expectorants and mucolytics), diagnostic agents, diagnostic imaging agents, diuretics, dopaminergics (antiparkinsonian agents), haemostatics, immunosuppressive cyclic oligopeptides, immuriological agents, lipid regulating agents, muscle relaxants, parasympathomimetics, parathyroid calcitonin and biphosphonates, prostaglandins, radiopharmaceuticals, sex hormones (including steroids), antiallergic agents, stimulants and anorexics, sympathomimetics, thyroid agents, vasidilators and xanthines. Preferred drug substances include those intended for oral administration and intravenous administration. A description of these classes of drugs and a listing of species within each class can be found in Martindale, The Extra Pharmacopoeia, Twenty-ninth Edition, The Pharmaceutical Press, London, 1989. More specific examples of drug substances useful in the practice of the present invention include but are not limited to danazol, cyclosporine, nifedipine, carbamazepine, naproxen, triamcinolone and its salts, hydrocortisone and its salts, prednisone and its salts, phenylbutazone, betamethasone and its salts, dexamethasone and its salts, 17-β estradiol, ketoprofen, verapamil, ketoconazole, mefenamic acid, and metronidazole.

The organic solvent into which the drug is dissolved can be any organic solvent which dissolves the drug to an adequate level. Preferably, the organic solvent dissolves the drug to a level of 0.1 weight percent or more, and more preferably to a level of 1.0 weight percent or more. The organic solvent is advantageously immiscible with water. Suitable organic solvents include diethylether, methylene chloride, ethyl acetate, dimethylether, perfluoroalkanes and isomers thereof, partially fluorinated solvents with or without other functional groups, and other organic solvents with boiling points below approximately 70° C., and combinations thereof.

In one embodiment, the drug/organic mixture further contains a particle stabilizer. Stabilization is defined herein to mean that the resulting drug particles do not grow substantially, and do not crystallize excessively. In this regard, a particle stabilizer is defined herein to mean a substance that substantially inhibits particle growth and substantially inhibits crystallization of the drug particles. The particle stabilizer can be water soluble or organic soluble, although, if the particle stabilizer is water soluble, bioavailability may be enhanced to an even greater degree. Particle stabilizers can also act as absorption enhancers in order to increase bioavailability of the drug particles.

The particle stabilizer present in the organic can contribute to stabilization of the particle in the aqueous phase. Examples of particle stabilizers include phospholipids, surfactants, either low molecular weight or polymeric, vesicles, polymers, including copolymers and homopolymers and biopolymers, and/or dispersion aids. The particle stabilizer can be nonionic, anionic, cationic or zwitterionic. Suitable surfactants include gelatin, casein, lecithin, (phosphatides), gum acacia, cholesterol, tragacanth, stearic acid, benzalkonium chloride, calcium stearate, glyceryl monostearate, cetostearyl alcohol, cetomacrogol 1000, polyoxyethylene castor oil derivatives, polyoxyethylene sorbitan fatty acid esters, for example, the commercially available Tweens, polyethylene glycols, copolymers of polyethylene glycol and polypropylene glycol, polyoxyethylene stearates, colloidal silicon dioxide, phosphates, sodium dodecylsulfate, carboxymethlcellulose calcium, carboxymethylecellulose sodium, methylcellulose, hydroxyethylcellulose, hydroxypropylcellulose, hydroxypropylmethylcellulose phthalate, noncrystalline cellulose, magnesium aluminum silicate, triethanolamine, polyvinylalcohol, sodium lauryl sulfate (SLS), polyvinylpyrrolidone (PVP), bile salts.

Referring again to FIG. 1, the drug/organic mixture is fed through feed line 12 to a sprayer, where the drug/organic mixture is sprayed into an aqueous solution contained in tank 13. The drug/organic mixture is sprayed at or below the liquid level of the aqueous solution in tank 13.

In one alternative embodiment of the present invention, a portion of the aqueous solution can be sprayed together with the drug/organic mixture into the remaining portion of the aqueous solution. In such an embodiment, the nozzle should be designed so as to allow the spraying of two streams simultaneously. In such an embodiment, the level of the aqueous solution in tank 13 can be controlled by, for example, an overflow, such that a continuous slurry of particles results. The slurry of particles can then undergo further processing to result in the final drug particles.

Figure 2:
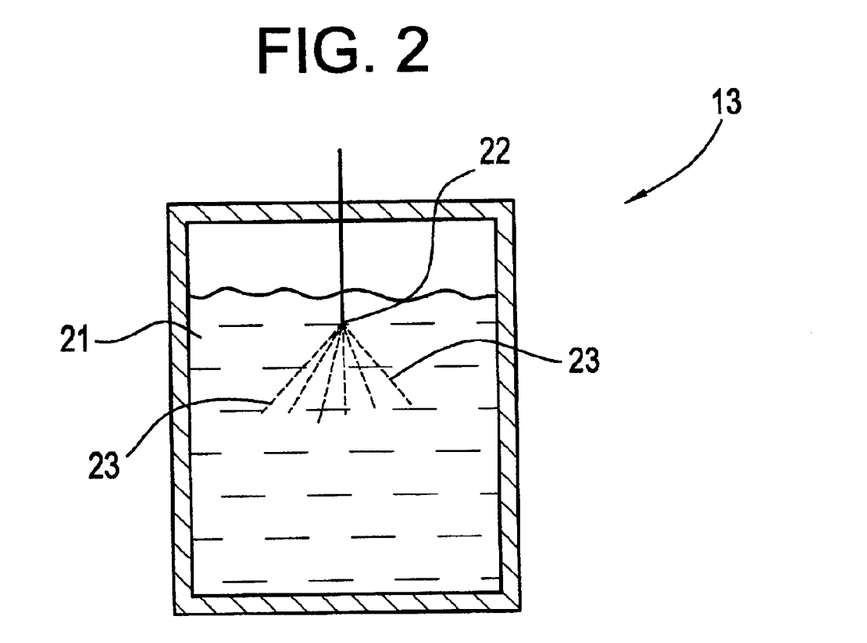
FIG. 2 is a cross-sectional view of a vessel useful in the process of the present invention.

FIG. 2 is a cross-sectional view of tank 13 containing aqueous solution 21. In a preferred embodiment, aqueous solution 21 contains at least one particle stabilizer. Suitable particle stabilizers include those listed above for inclusion in the drug/organic mixture. The specific particle stabilizer or particle stabilizers selected for use in the aqueous solution 21 can be the same or can be different from the particle stabilizer(s) in the drug/organic mixture. The weight ratio of drug to total particle stabilizer is from 0.01:1 to 10:1, preferably from 0.05:1 to 7:1 and more preferably from 0.1:1 to 4:1.

The drug/organic mixture is sprayed at or below the liquid level in tank 13 through atomizer 22 to form a jet comprising droplets 23. The jet results in intense mixing between the drug/organic mixture droplets and the aqueous solution. Thus, as the drug/organic mixture is sprayed through atomizer 22, the organic solvent is concurrently evaporated into the aqueous solution 21 to form an aqueous dispersion of the drug particles. In this manner, evaporation of the organic solvent is occurring rapidly with the spraying and stabilization of the drug particles by the excipients in the aqueous solution. Evaporation of the organic solvent occurs below the surface of the aqueous solution.

Atomizer 22 can be any device that is capable of breaking up a bulk liquid into droplets. Suitable devices useful as atomizers include pressure nozzles, venturi nozzles, vibrating orifices, ultrasonic spray nozzles, rotating cups or disks, bubble caps or grids, or perforated plates.

The atomization of the evaporating organic solution into small droplets in the water and the intensity of the spray produce intense mixing between the growing drug particles and the water-soluble stabilizers and excipients. The rapid evaporation of the organic solvent produces large supersaturation of the drug and rapid precipitation. The rapid precipitation of the drug has the potential to produce amorphous instead of crystalline particles as the time frame is too short for crystallization. The hydrophilic stabilizers remain solvated by water during the evaporation of the organic solvent. Thus, the stabilizers cover the growing drug particles and inhibit growth. The morphology and particle size of the resulting particles may be controlled by varying the flow rate, nozzle geometry, concentration of drug and stabilizer and the nature of the stabilizer(s).

The temperature of the drug/organic mixture is at a level which allows for rapid evaporation of the solvent. Typically, this temperature will be at least 50 degrees centigrade (° C.) below the normal boiling point of the organic solvent to 80° C. above the normal boiling point of the organic solvent. If the temperature of the drug/organic mixture is at or above its normal boiling point, feed line 12 must be at sufficient pressure to maintain a liquid phase.

The temperature of the aqueous phase is preferably at least 10° C., more preferably at least 50° C., and even more preferably at least 70° C. The upper temperature limit will depend upon the operating pressure, but is preferably low enough so as not to degrade the drug, but high enough to evaporate the solvent but not evaporate too much of the water. In a preferred embodiment, the temperature is less than 120° C., more preferably less than 95° C., and even more preferably less than 85° C. The pressure of the aqueous solution can be at ambient pressure, below ambient pressure to facilitate evaporation or above ambient pressure.

In the present invention, the drug particles are produced in a liquid aqueous phase rather than a gas phase. Therefore, the particle growth is inhibited by aqueous stabilizers that do not precipitate. The dissolution rates of the drug particles coated with water soluble stabilizers may be expected to be high since the dispersions come from an aqueous phase. In the present invention the particle formation stage is distinct from stage in which the aqueous solution is dried. Therefore the present invention can provide greater control over particle size.

The average particle diameter of the particles in the aqueous dispersion are from 50 nanometers to 20 microns, more preferably from 100 nanometers to 5 microns, and even more preferably from 200 nanometers to 1 micron. The drug particles are not necessarily spherical. Average particle diameter can be measured using any technique known to those skilled in the art, such as sedimentation field flow fractionation, photon correlation spectroscopy, disk centrifugation or dynamic light scattering techniques.

An advantage of the present invention is the narrow polydispersity, also referred to as particle size distribution, that results. The particle size distribution is typically monomodal, with narrow size ranges.

As an additional advantage, it is believed that drug particles prepared according to the present invention can exhibit reduced crystallinity as compared to the bulk, unprocessed drug. Such reduced crystallinity can lead to increased dissolution rates and bioavailability.

The process of the present invention desirably further comprises the step of recovering the drug particles. In one embodiment, recovering the drug particles comprises removing the water from the particles. Removing the water can be performed using any technique known to those skilled in the art, including spray drying, spray freeze drying, gellation, defined as gelling the particles within a polymeric matrix, lyophilization, drying with cold air, and filtration.

Advantageously, excipients can be added to either the drug/organic mixture or to the aqueous solution, either before or after the drug particles are formed, in order to enable the drug particles to be homogeneously admixed for appropriate administration. Suitable excipients include polymers, absorption enhancers, solubility enhancing agents, dissolution rate enhancing agents, stability enhancing agents, bioadhesive agents, controlled release agents, flow aids and processing aids. More particularly, suitable excipients include cellulose ethers, acrylic acid polymers, and bile salts. Other suitable excipients are described in detail in the Handbook of Pharmaceutical Excipients, published jointly by the American Pharmaceutical Association and The Pharmaceutical Society of Great Britain, the Pharmaceutical Press, 1986, which is incorporated by reference herein. Such excipients are commercially available and/or can be prepared by techniques known in the art.

The following examples are for illustrative purposes only and are not intended to limit the scope of the claimed invention. Percentages are in weight percents unless otherwise stated.

EXAMPLES

For the following examples, the apparatus shown in FIG. 1 is used. The drug/organic mixture was fed via a Constametric 3200 HPLC pump through a preheating coil into a 30 mL receiving tank containing the required amount of aqueous solution. The nozzle used for the spraying was made by cutting 1/16" stainless steel tubing to form an elliptical conical geometry at the end. The end of the tube was filed to obtain the desired flow rate. Nitrogen was continuously flowed downward to break up foam in cases where it formed. For all of the examples, particle size was measured by dynamic light scattering techniques within 4 hours of the spray.

Dissolution testing for the following examples was carried out using a Vankel dissolution apparatus following the USP Apparatus II paddle method. During all dissolution tests, to ensure sink conditions, only 10–30 percent of the saturation solubility of the drug was added to the dissolution apparatus. The appropriate amount of final drug preparation was weighed and added to 900 ml of distilled water. Each sample was stirred at 50 rpm using a paddle-type stirrer. The dissolution apparatus was maintained at 37° C. throughout the experiment. Samples in the amount of 5 ml were automatically withdrawn at 10, 20, 30 and 60 minute intervals. These samples were filtered using a 0.45 µm filter (Gelman GHP disc 0.45 µm, VWR). To ensure that no precipitation occurred during HPLC analysis, 0.5 ml of organic solvent was added to 3 ml of filtered sample. This organic solvent was preferably the organic component in mobile phase (acetonitrile). These were mixed using a vortex mixer at high speed for approximately 10 seconds and then refiltered using a 0.45 µm filters into a HPLC vial for analysis. HPLC analysis was different for each drug and the exact methods being modified from those suggested in 'HPLC methods for pharmaceutical analysis' by George Lunn and Normnan R. Schmuff, John Wiley & Sons, NY, 1997.

Examples 1–8

The drug was cyclosporine, the organic was diethylether, and the concentration of the drug/organic mixture was 5.0 weight percent cyclosporine in diethylether. For the aqueous solution, Tween-80, a polyoxyethylene sorbitan monolaurate(ACROS) was a surfactant which was used as the particle stabilizer. The drug/organic mixture was sprayed into 10 mL of aqueous solution at a rate of 1 ml/min. Table A lists processing parameters and the resulting particle sizes.

Table A

| Ex | Drug/organic temp. (° C.) | Aqueous temp (° C.) | Spray time (min) | Tween-80 conc (wt percent) | Median particle size (nm) | percent particles < median size |
|---|---|---|---|---|---|---|
| 1 | 65 | 55 | 10 | 1 | 470 | 11 |
| 2 | 65 | 55 | 10 | 1 | 608 | 64 |
| 3 | 65 | 65 | 10 | 1 | 1114 | 61 |
| 4 | 65 | 65 | 10 | 1 | 759 | 41 |
| 5 | 70 | 65 | 10 | 1 | 706 | 33 |
| 6 | 70 | 65 | 10 | 1 | 796 | 43 |
| 7 | 70 | 65 | 10 | 1 | 932 | 50 |
| 8 | 70 | 65 | 20 | 5 | 322 | 14 |

Examples 9–13

The drug was cyclosporine, the organic was diethylether, and the concentration of the drug/organic mixture was as shown below in Table B. For the aqueous solution, phosphatidyl choline (10 wt percent), a Sigma egg lecithin, 60 percent pure, was a surfactant used as a particle stabilizer. The drug/organic mixture was sprayed into 10 mL aqueous solution at a rate of 1 ml/min. The temperature of the aqueous solution is 75° C., while the drug/organic mixture was sprayed into the aqueous solution at a temperature of 75° C. Table B lists some processing parameters and the resulting particle sizes.

TABLE B

| Ex | Drug conc in organic soln (wt percent) | Spray time (min) | Drug conc in aqueous (mg/ml water) | Drug/ surfactant ratio | Particle size range (nm) |
|---|---|---|---|---|---|
| 9 | 1 | 20 | 14.5 | 0.13 | 135–390 |
| 10 | 2 | 19 | 30.8 | 0.28 | 120–575 |
| 11 | 5 | 10 | 37.1 | 0.33 | 90–300 |
| 12 | 5 | 10 | 34.9 | 0.32 | 215–590 |
| 13 | 10 | 6 | 29.7 | 0.30 | 170 |

Examples 14–16

The drug was cyclosporine (5 wt percent), the organic solvent was that listed in Table C below. For the aqueous solution, Poloxamer 407 (1 wt percent), also known as Lutrol-F127, a poly(ethylene)-poly(propylene) block polymer consisting of 73 percent of polyethelene glycol and 27 percent polypropylene glycol with an average molecular weight of 12,000 (BASF), was a surfactant used as a particle stabilizer. The drug/organic mixture was sprayed into 25 mL aqueous solution at a rate of 1 ml/min. The temperatures of the aqueous solution and of the drug/organic mixture were 75° C. Table C lists some processing parameters and the resulting particle sizes.

TABLE C

| Ex | Organic Solvent | Drug conc in aqueous (mg/ml water) | Drug/ surfactant ratio | Particle size range (nm) |
|---|---|---|---|---|
| 14 | Diethyl Ether | 15 | 1.5 | 320–1000 |
| 15 | Dichloromethane | 17.8 | 1.78 | 160–345 |
| 16 | Dichloromethane | 14.8 | 1.48 | 196–202 |

Examples 17–21

The drug was danazol, and the solvent was methylene chloride. The particle stabilizer in the aqueous solution is listed below in Table D. In all cases, the concentration of the particle stabilizer in aqueous solution was 1 weight percent. The drug/organic mixture (2 wt percent drug) was sprayed into the aqueous solution at a rate of 2 ml/minute for 5 minutes. The temperature of both the aqueous solution and the drug/organic mixture was 75° C. The drug/surfactant ratio was 1.06.

TABLE D

| Ex | Particle stabilizer | Particle size range (nm) |
|---|---|---|
| 17 | Sodium lauryl sulfate | 370–415 |
| 18 | Poly (vinyl pyrolidone) | 140–280 |
| 19 | Poly (vinyl pyrolidone) | 315–450 |
| 20 | Poloxamer | >1000 |
| 21 | Myrj 52 | >1000 |

Myrj is polyoxyethylene monostearate.

Examples 22–26

The drug was Carbamazepine, and the solvent was methylene chloride. The concentration of drug in the organic was 2 weight percent. The particle stabilizer in the aqueous solution is listed below in Table E. In all cases, the concentration of the particle stabilizer in aqueous solution was 1 weight percent. The drug/organic mixture was sprayed into the aqueous solution at a rate of 2.5 ml/min. The temperature of both the aqueous solution and the drug/organic mixture was 75° C. The drug/surfactant ratio was 1:30.

TABLE E

| Ex | Particle stabilizer | Particle size range (nm) |
| --- | --- | --- |
| 22 | Sodium lauryl sulfate (SLS) | >7000 |
| 23 | Poly (vinyl pyrolidone) (PVP) | 320–1000 |
| 24 | Polyethylene glycol | 290–550 |
| 25 | Poloxamer | >1000 |
| 26 | Myrj 52 | >1000 |

Examples 27–29

Figure 3:
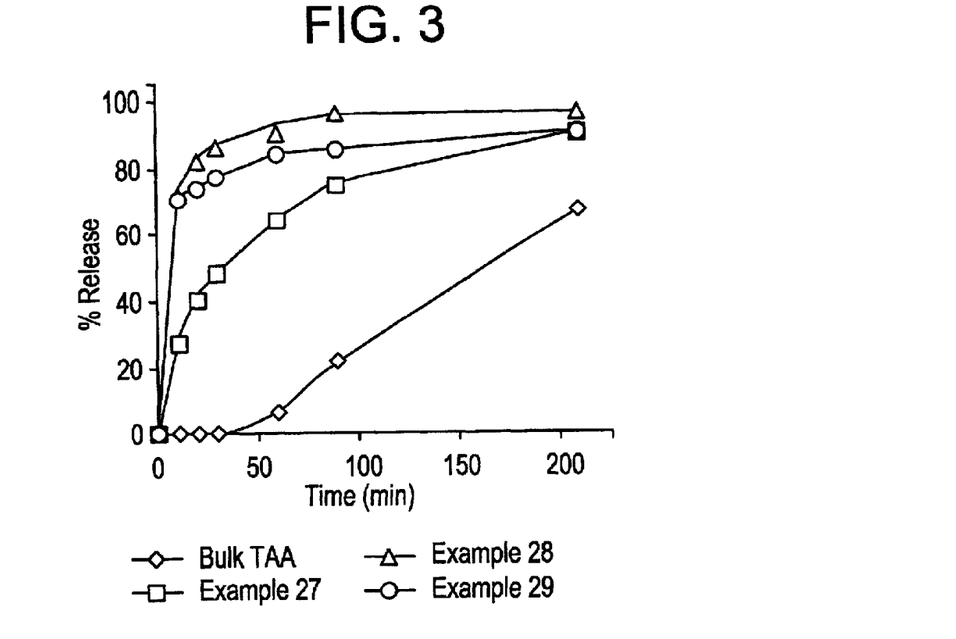
FIGS. 3–4 are graphs showing improved dissolution rates for particles of the present invention.

The drug was Triamcinolone acetonide, also referred to herein as TAA, and the solvent was methylene chloride. The concentration of drug in the organic was 0.5 weight percent. The particle stabilizers in the aqueous solution and the organic solution are listed in Table F. In all cases the concentration of the particle stabilizer in the aqueous solution was 1 weight percent and in the organic solution was 0.5 weight percent. The volume of the aqueous solution was 15 ml. In all cases the resulting aqueous drug suspension was poured into a hydroxypropylmethyl cellulose (HPMC) (grade E-5), thoroughly mixed by hand, poured into a glass crystallization dish and vacuum dried for at least 10 hours at temperatures ranging from 40–60° C. and a vacuum level of about 30 inches of Hg. The resulting solids were mechanically ground to a powder and dissolution studies were performed on these powders. The results of these dissolution tests were compared with that for bulk TAA. The results shown in FIG. 3 indicate the increased dissolution rates of TAA processed according to the present invention.

TABLE F

| Ex | Organic stabilizer | Aqueous stabilizer | Amount of HPMC added for gellation (g) |
| --- | --- | --- | --- |
| 27 | PVP K-15 | Deoxycholic acid | 3 |
| 28 | Poloxamer 407 | PVP K-15 | 2 |
| 29 | Poloxamer 407 | Deoxycholic acid | 2 |

Examples 30–32

Figure 4:
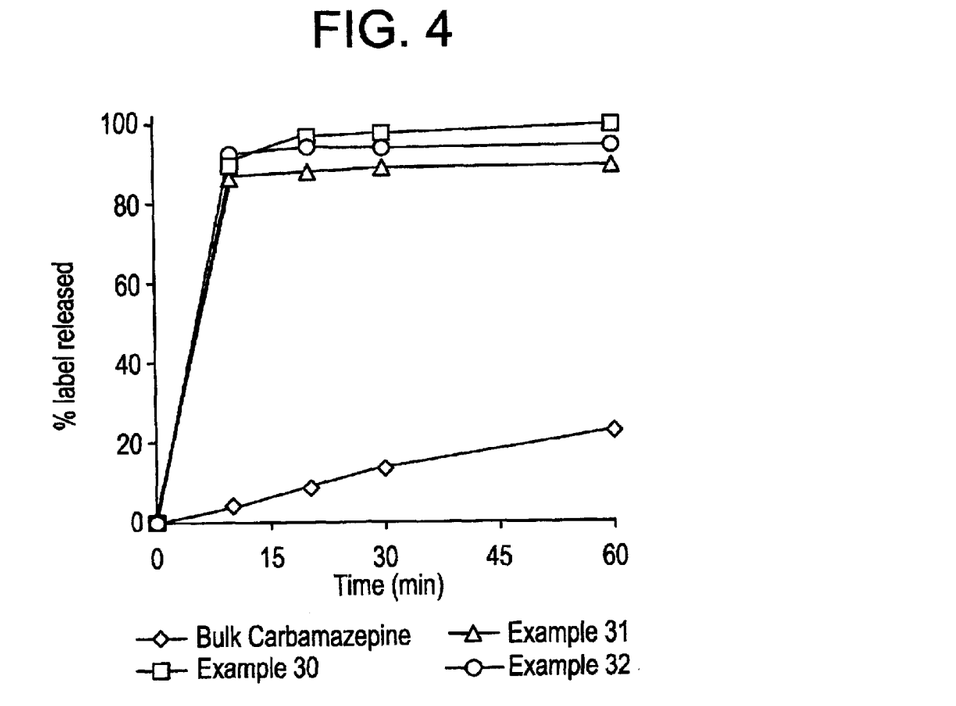

The drug was carbamazepine and the solvent was methylene chloride. The temperature of the drug/organic mixture and the receiving aqueous solution was 87° C. The concentration of drug in the organic was 1.0 weight percent. The particle stabilizers in the aqueous solution are listed in Table G. In all cases the concentration of the particle stabilizer in the aqueous solution was 2 weight percent and the organic solution contains, in addition to the drug, 0.5 weight percent Poloxamer 407. The volume of the aqueous solution was 20 ml. In all cases the resulting aqueous drug suspension was sprayed into liquid nitrogen and the frozen particles were then lyophilized for 24 hours. The resulting powder was thoroughly mixed and dissolution studies were performed on these powders. The results of these dissolution tests were compared with those for bulk carbamazepine. The results shown in FIG. 4 clearly indicate the increased dissolution rates of carbamazepine processed according to the present invention over the bulk unprocessed carbamazepine. The crystallinity of these powders was also studied, with the result being a reduction in crystallinity as compared to the bulk drug.

TABLE G

| Ex | Aqueous stabilizer |
| --- | --- |
| 30 | Deoxycholic acid |
| 31 | PVP K-15 |
| 32 | SLS |

Example 33

Figure 5:
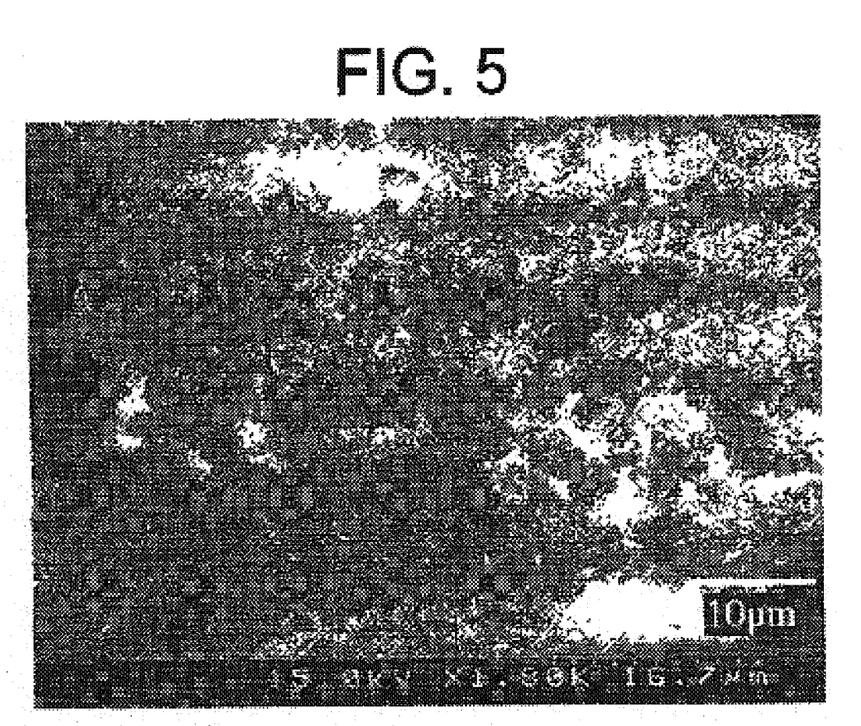
FIG. 5 is an SEM showing reduced crystallinity of the particles of the present invention.

The drug was carbamazepine and the solvent was methylene chloride. The temperature of the drug/organic mixture and the receiving aqueous solution was 87° C. The concentration of drug in the organic was 1.0 weight percent. The particle stabilizer in the aqueous solution was 2 weight percent deoxycholic acid and that in the organic solution was 0.5 weight percent Poloxamer 407. The organic solution was sprayed at 2 ml/min for 27 minutes into 50 ml of the aqueous deoxycholic acid solution. The suspension was immediately spray dried in a Buchi 190 spray dryer where an inlet temperature of 145–150 degrees C. and an outlet temperature of 90–95° C. were maintained. The resulting dry powder was collected, and an SEM micrograph of this powder is shown in FIG. 5. The Figure shows no crystalline particles indicating the amorphous nature of the drug produced using EPAS.

Examples 34–37

Figure 6:
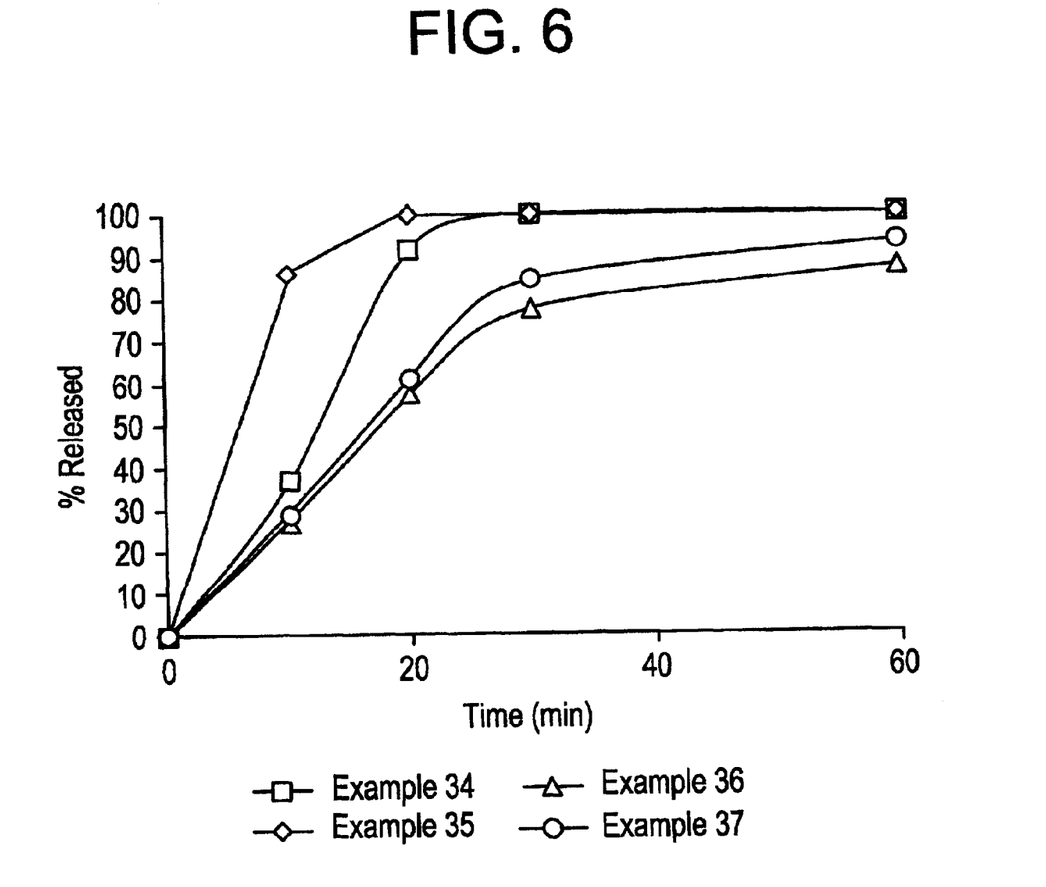
FIG. 6 is a graph showing improved dissolution rates for particles of the present invention.

The drug was nifedipine and the solvent was methylene chloride. The concentration of drug in the organic was 1.0 weight percent. In all cases the stabilizer in the aqueous solution was poly(vinyl alcohol) (PVA). The volume of the aqueous solution was 20 ml. Table H lists excipients added to the aqueous solution in addition to the PVA. In all cases the resulting aqueous drug suspension was rapidly frozen by dipping the sample container in liquid nitrogen and then lyophilized for 24 hours. The resulting powder was thoroughly mixed and dissolution studies were performed on these powders. The results of these dissolution tests were compared with that for bulk nifedipine. The results, shown in FIG. 6, clearly indicate the increased dissolution rates of EPAS processed nifedipine over the bulk unprocessed nifedipine. The crystallinity of these powders was also studied using X-ray diffraction patterns, with the result being a reduction in crystallinity of the drug processed according to the present invention as compared to the bulk drug.

TABLE H

| Ex | Excipients in aqueous solution |
| --- | --- |
| 34 | 1.5 wt percent PVP K40 |
| 35 | 1.5 wt percent SLS |
| 36 | 1 wt percent Poloxamer 407 |
| 37 | 1 wt percent PVP K15 |

Examples 38–39

The drug was ketoprofen and the solvent was methylene chloride. The temperature of the sprayed drug/organic mixture and the receiving aqueous solution was 87° C. The concentration of drug in the organic was 1.0 weight percent. The particle stabilizers in the aqueous solution are listed in Table J. In all cases the concentration of the particle stabilizer in the aqueous solution was 2 weight percent and the organic solution contains, in addition to the drug, 0.5 weight percent Poloxamer 407. The volume of the aqueous solution was 20 ml. In all cases the resulting aqueous drug suspension was rapidly frozen by dipping the sample container in liquid nitrogen and then lyophilized for 24 hours. Crystallinity studies were performed on these powders using X-ray diffraction patterns, and were compared with that for bulk ketoprofen, which resulted in the processed powder exhibiting amorphous character as opposed to the bulk ketoprofen.

TABLE J

| Ex | Aqueous stabilizer |
|---|---|
| 38 | Deoxycholic acid |
| 39 | SLS |

What is claimed is:

1. A method for preparing an aqueous dispersion of poorly water soluble drug particles comprising the steps of:
  dissolving a drug in at least one organic solvent to form a drug/organic mixture;
  spraying the drug/organic mixture via an atomizing device into an aqueous solution, wherein at least one particle stabilizer is originally present in the aqueous solution, the drug/organic mixture or both the aqueous solution and the drug/organic mixture, and wherein the drug/organic mixture is sprayed below the liquid level of the aqueous solution; and
  concurrently evaporating the organic solvent in the presence of the aqueous solution to form an aqueous dispersion of the drug particles, thereby causing the stabilizer to cover the drug particles as the organic solvent is evaporated.

2. The method according to claim 1 wherein the particle stabilizer is a surfactant, a polymer, or a dispersion aid.

3. The method according to claim 2 wherein the particle stabilizer is an absorption enhancer for bioavailability.

4. The method according to claim 2 wherein the particle stabilizer in the aqueous solution is different than the particle stabilizer in the drug/organic mixture.

5. The method according to claim 2 wherein the particle stabilizer in the aqueous solution is the same as the particle stabilizer in the drug/organic mixture.

6. The method according to claim 1 wherein the weight ratio of drug to particle stabilizer is from 0.1:1 to 10:1.

7. The method according to claim 1 wherein the particle stabilizer is selected from the group consisting of surfactants, phospholipids, copolymers, and homopolymers.

8. The method according to claim 7, wherein the particle stabilizer is nonionic, anionic, cationic or zwitterionic.

9. The method according to claim 1 further comprising the step of adding one or more excipients.

10. The method according to claim 9 wherein the excipients are originally present in the aqueous solution, the drug/organic mixture, or both.

11. The method according to claim 9 wherein the excipients are added to the aqueous dispersion after the drug particles are formed.

12. The method according to claim 9 wherein the excipients are selected from the group consisting of polymers, absorption enhances, solubility enhancing agents, dissolution rate enhancing agents, stability enhancing agents, bioadhesive agents, controlled release agents, flow aids and processing aids.

13. The method according to claim 1 wherein the temperature of the drug/organic mixture is at a level which allows for rapid evaporation of the solvent.

14. The method according to claim 1 wherein the temperature of the aqueous phase is from about 10° C. to 120° C.

15. The method according to claim 1 wherein a portion of the aqueous solution is sprayed together with the drug/organic mixture into the remaining portion of the aqueous solution.

16. The method according to claim 1 further comprising the step of recovering the particles.

17. The method according to claim 16 wherein recovering the particles comprises removing the water from the particles.

18. The method according to claim 17 wherein removing the water comprises spray drying, spray freezing, gellation, lyophilization, drying with cold air, or filtration.

19. The method according to claim 1 wherein the average particle diameter of the particles in the aqueous dispersion are from 50 nanometers to about 20 microns.

20. The method according to claim 1 wherein the spraying occurs through a nozzle.

21. The method according to claim 20 wherein the nozzle produces a jet comprising fine droplets.

22. The method according to claim 21 wherein the jet results in intense mixing between the drug/organic mixture droplets and the aqueous solution.

23. Drug particles prepared according to the process of claim 7.

24. An aqueous dispersion of poorly water soluble drug particles having an average particle diameter of from 50 nanometers to 20 microns, the aqueous dispersion being prepared by a process comprising the steps of:
  dissolving the drug in at least one organic solvent to form a drug/organic mixture;
  spraying the drug/organic mixture into an aqueous solution, wherein at least one particle stabilizer is originally present in the aqueous solution, the drug/organic mixture or both the aqueous solution and the drug/organic mixture, and wherein the drug/organic mixture is sprayed below the liquid level of the aqueous solution; and
  concurrently evaporating the organic solvent in the presence of the aqueous solution to form an aqueous dispersion of the drug particles, thereby causing the stabilizer to cover the drug particles as the organic solvent is evaporated.

25. A method for preparing an aqueous dispersion of poorly mater soluble drug particles comprising the steps of:
  dissolving a drug in at least one organic solvent to form a drug/organic mixture;
  spraying the drug/organic mixture via an atomizing device into an aqueous solution, wherein at least one particle stabilizer is originally present in the aqueous solution, the drug/organic mixture or both the aqueous solution and the drug/organic mixture, and wherein the drug/organic mixture is sprayed below the liquid level of the aqueous solution; and
  rapidly evaporating the organic solvent in the presence of the aqueous solution to form an aqueous dispersion of the drug particles, thereby causing the stabilizer to cover the drug particles as the organic solvent is evaporated.

* * * * *